United States Patent [19]

Wikel et al.

[11] 4,008,243

[45] Feb. 15, 1977

[54] ANTIVIRAL THIAZOLINYL OR THIAZINYL BENZIMIDAZOLE ESTERS

[75] Inventors: James H. Wikel, Greenwood; Charles J. Paget, Indianapolis, both of Ind.

[73] Assignee: Eli Lilly and Company, Indianapolis, Ind.

[22] Filed: Nov. 19, 1975

[21] Appl. No.: 633,203

[52] U.S. Cl. .................. 260/306.7 T; 260/243 R; 260/309.2; 260/454; 424/246; 424/27 B
[51] Int. Cl.² ...................................... C07D 417/04
[58] Field of Search ............ 260/306.7 R, 306.7 T, 260/243 R

[56] References Cited

UNITED STATES PATENTS

| 3,749,717 | 7/1973 | Haugwitz et al. | 260/243 R |
| 3,825,537 | 7/1974 | Haugwitz et al. | 260/306.7 T |
| 3,833,574 | 9/1974 | Haugwitz et al. | 260/306.7 T |

*Primary Examiner*—Donald G. Daus
*Assistant Examiner*—David E. Wheeler
*Attorney, Agent, or Firm*—James L. Rowe; Everet F. Smith

[57] ABSTRACT

Certain thiazolinyl or thiazinyl benzimidazole ester compounds are useful as antiviral agents.

15 Claims, No Drawings

ANTIVIRAL THIAZOLINYL OR THIAZINYL BENZIMIDAZOLE ESTERS

BACKGROUND OF THE INVENTION

The incidence of viral upper respiratory disease is immense. It has been estimated that nearly a billion cases annually appear in the United States alone. Studies performed in England (Tyrell and Bynoe, 1966) indicated that 74 percent of persons having colds were infected with rhinoviruses. Because more than 80 strains of rhinoviruses are already identified, the development of a practical rhinovirus vaccine is not feasible. In this, chemotherapy appears to the more desirable approach.

The ability of chemical compounds to suppress the growth of viruses in vitro is readily demonstrated by using a virus plaque suppression test similar to that described by Siminoff, Applied Microbiology, 9 (1), 66(1961).

It is an object of this invention to provide novel thiazolinyl or thiazinyl benzimidazole esters which are useful in suppressing the growth of viruses, particularly Coxsackie, echo, Mengo, polio, rhinoviruses and influenza.

Certain thiazolinyl or thiazinyl benzimidazole compounds are disclosed in the following references:

U.S. Pat. No. 3,749,717 discloses 1-thiazolinyl- or 1-thiazinyl-2-heterocyclic-benzimidazoles useful as anthelminic and anti-inflammatory agents.

U.S. Pat. No. 3,825,537 discloses 1-thiazolinyl or 1-thiazinyl-2-aminobenzimidazoles useful as anthelmintic and anti-inflammatory agents.

U.S. Pat. No. 3,833,574 discloses a method of preparing 1-thiazolinyl- or 1-thiazinylbenzimidazolin-2-ones which are anti-inflammatory agents.

Derwent 26199W/16 discloses 1-thiazolinyl- or 1-thiazinyl-2-phenylbenzimidazoles useful as anthelmintic agents.

There is no known prior art reference to antiviral activity of thiazolinyl or thiazinyl benzimidazole esters.

SUMMARY OF THE INVENTION

This invention concerns the pharmacologically useful benzimidazole ester compounds represented by the formula

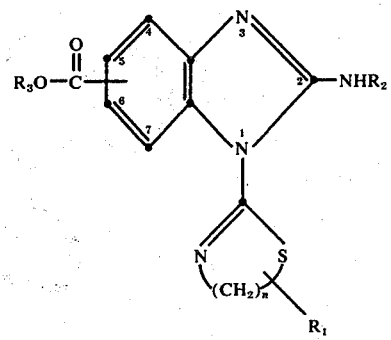

wherein $R_1$ is hydrogen, $C_1$–$C_3$ alkyl, benzyl or phenyl;
$R_2$ is hydrogen, formyl, acetyl or propionyl;
$R_3$ is $C_1$–$C_8$ alkyl, allyl, propargyl, $C_3$–$C_7$ cycloalkyl, ($C_3$–$C_7$ cycloalkyl)methyl, 1-($C_3$–$C_7$ cycloalkyl)ethyl, benzyl, α-methylbenzyl or phenyl;

is at the 5 or 6 position; and
n is 2 or 3.

The compounds of the invention represented by the above formula are especially effective in suppressing the growth of viruses selected from the group consisting of Coxsackie, echo, Mengo, polio, rhinoviruses and influenza. An antivirally effective amount of a thiazolinyl or thiazinyl benzimidazole ester represented by the Formula I can be administering to mammals susceptible to said virus infection including humans.

DETAILED DESCRIPTION AND PREFERRED EMBODIMENT

The present invention relates to novel thiazolinyl and thiazinyl benzimidazole ester compounds which are useful in suppressing the growth in mammals of certain viruses including Coxsackie, echo, Mengo, polio, and influenza. The novel ester compounds provided by this invention are prepared by reacting the salt (III) of a tautomeric benzimidazole ester compound (II) with an aliphatic haloalkylisothiocyanate (IV), X—(CH$_2$)$_n$—NCS, optionally substituted on the carbon chain with $R_1$ groups, wherein $R_1$, $R_2$, $R_3$ and n are as defined above and X is chloro or bromo, to yield a compound according to Formula V (Formula I above wherein $R_2$ is hydrogen).

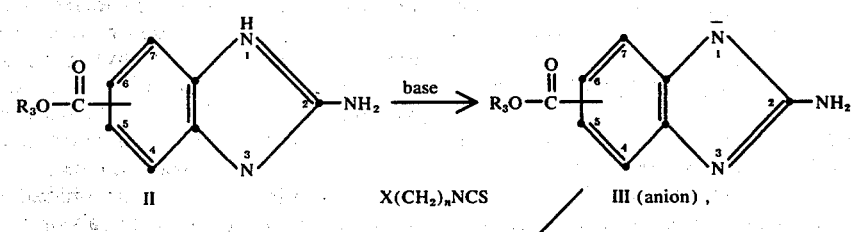

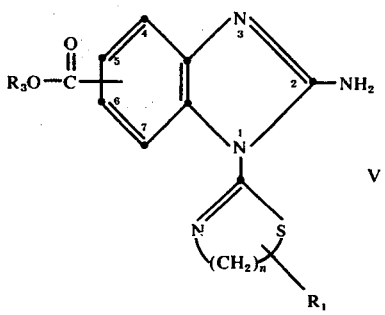

V

The term "tautomeric benzimidazole" refers to a benzimidazole ester compound used as a starting material in the above reaction and which can be substituted on either nitrogen atom with a hydrogen atom. The benzimidazole reactant, unsubstituted on nitrogen and bearing an

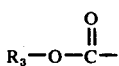

substituent group at the 5-position of the benzene moiety has a corresponding tautomeric form with which it is in equilibrium wherein the substituent resides alternatively at the 6-position. The isomer mixture can be indicated by numbering the alternate positions as 5(6). As a consequence of such tautomerism, the 5(6)-substituted tautomeric benzimidazole salt (III) can react on either nitrogen with the haloalkylisothiocyanate (IV) to produce an isomeric mixture containing both the 5- or 6-substituted thiazolinyl or thiazinyl benzimidazole (V), named herein as 5(6)-substituted compounds.

The following definitions refer to the various terms used throughout this disclosure. The term $C_1$–$C_8$ alkyl refers to the straight and branched alkyl radicals of one to eight carbon atoms including methyl, ethyl, propyl, isopropyl, butyl, isobutyl, sec-butyl, tert-butyl, amyl, isoamyl, sec-amyl sec-isoamyl (1,2-dimethylpropyl), tert-amyl (1,1-dimethylpropyl), neopentyl, hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 1-ethylpentyl, 2,2-dimethylpentyl, 3,3-dimethylpentyl, 4,4-dimethylpentyl, 1,2-dimethylpentyl, 1,3-dimethylphenyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl) and the like. The term $C_1$–$C_8$ includes within its definition the term $C_1$–$C_3$ alkyl.

The term $C_3$–$C_7$ cycloalkyl refers to the saturated alicyclic rings of three to seven carbon atoms such as cyclopropyl, methylcyclopropyl, cyclobutyl, cyclopentyl, cyclohexyl, 1-, 2-, 3-, or 4-methylcyclohexyl and cycloheptyl. The term $C_3$–$C_7$ cycloalkylmethyl refers to a methyl radical substituted with saturated alicyclic rings of three to seven carbon atoms as exemplified in the term $C_3$–$C_7$ cycloalkyl, such as cyclopropylmethyl, cyclobutymethyl, cyclopentylmethyl, cyclohexylmethyl, cycloheptylmethyl and the like. The term $C_3$–$C_7$ cycloalkyl alcohol refers to cyclopropanol, cyclobutanol, cyclopentanol, cyclohexanol and cycloheptanol. The term $C_3$–$C_7$ cycloalkylmethanol refers to methanol substituted on carbon with saturated alicyclic rings of three to seven carbon atoms such as cyclopropanemethanol, cyclobutanemethanol, cyclopentanemethanol, cyclohexanemethanol, and cycloheptanemethanol. These $C_3$–$C_7$ alicyclic methanols are available from the corresponding $C_3$–$C_7$ alicyclic carboxaldehydes by reduction. The term 1-($C_3$–$C_7$ cycloalkyl)ethanol refers to ethanol which is substituted on the carbon atom in the 1 position with saturated alicyclic rings of three to seven carbon atoms such as 1-cyclopropaneethanol, 1-cyclopentaneethanol, 1-cycloheptaneethanol and the like. These ethanols are available from the corresponding 1-($C_3$–$C_7$ cycloalkyl) methyl ketones by reduction. The term 1-($C_3$–$C_7$ cycloalkyl) ethyl refers to ethyl radicals substituted on the carbon atom in the 1 position with saturated alicyclic rings of three to seven carbon atoms.

The term thiazolinyl or thiazolin-2-yl refers to the $N_1$ moiety of Formula I wherein $n$ is 2 and indicates a 4,5-dihydrothiazole radical attached at the 2-position which may have substituent groups ($R_1$) in the 4 or 5 positions. The term thiazinyl or thiazin-2-yl refers to the $N_1$ moiety wherein $n$ is 3 and indicates a 5,6-dihydro-4H-1,3-thiazine radical attached at the 2-position which may be substituted on the 4,5 or 6positions by $R_1$ groups. Illustrative of the thiazinyl or thiazolinyl moieties which are included within the scope of this invention are those which can be substituted in the 4,5 or 6positions with methyl, ethyl, propyl, benzyl or phenyl groups.

The compounds of Formula V can be prepared by first converting the appropriately substituted benzimidazole reactant (II) into its salt (III) by employing a base such as metal hydrides; e.g., sodium hydride or potassium hydride; a metal amide; e.g., sodium amide; alkali metal alkoxides; e.g., sodium methoxide, potassium ethoxide or sodium butoxide and the like bases. Anion formation can be brought about in a variety of aprotic solvents such as aromatic hydrocarbons, e.g., benzene, toluene or xylene, or ethers such as ethyl ether, glyme or tetrahydrofuran at a temperature ranging from about 0° to about 150° C. for periods of about 1 hour to 24 hours. A slight excess of the base is desirable; thus the molar ratio of benzimidazole reactant to base can range from about 1:1 to 1:2.

The benzimidazole anion (III) reacts with an aliphatic haloalkylisothiocyanate (IV) to yield a thiourea intermediate in situ, which thiourea intermediate undergoes intramolecular alkylation on the sulfur atom to form a 1-thiazolinyl- or 1-thiazinylbenzimidazole product represented by Formula V. The molar ratio of the benzimidazole reactant (II) to haloalkylisothiocyanate (IV) can range from 1:1 to 1:1.5 and the reaction time can vary from about one to twenty-four hours at temperatures from about 25° to about 150° C. The methods and conditions for preparing the 1-thiazolinyl- or 1-thiazinylbenzimidazole products are analogous to those disclosed in U.S. Pat. Nos. 3,749,717 and 3,825,537.

The thiazolinyl or thiazinyl benzimidazole product may be isolated by conventional methods such as filtration followed by concentration of the filtrate to induce crystallization. Alternatively the reaction mixture can be evaporated to dryness and the residue treated with a suitable solvent such as acetone or methanol to separate and remove any insoluble material. The solution containing the product is concentrated to crystallize the product or is evaporated to give a second residue, which is dissolved in methanol for example. The benzimidazole compound is recovered by filtration or centrifugation.

The reaction of the tautomeric anion (III) with the haloalkylisothiocyanate generally provides a 1:1 mixture of 5(6)-isomers of thiazolinyl or thiazinyl benzimidazole product. The 5(6)-isomers are separated by fractional crystallization or by column chromatography. Usually the 6-isomer crystallizes first from a solution of the isomeric mixture. Individual isomers can be unambiguously characterized by their proton magnetic resonance spectra in the phenyl proton region (7.0 to 8.3 ppm).

The thiazolinyl or thiazinyl benzimidazole ester compounds represented by Formula I wherein $R_2$ is formyl, acetyl or propionyl can be prepared by reacting the 1-thiazolinyl- or 1-thiazinyl-2-aminobenzimidiazole esters (Formula V) with the anhydrides of acetic or propionic acid or the mixed anhydride of formic acid and acetic acid.

The required benzimidazole reactants (II) can be prepared from the appropriate o-phenylenediamine esters by methods known to the benzimidazole art.

For example 3,4-dinitrobenzoic acid can be reacted with oxalyl chloride and pyridine in benzene to provide the corresponding 3,4-dinitrobenzoyl chloride. This acid chloride is reacted with an appropriate carbinol; i.e., a straight or branched chain aliphatic alcohol of one to eight carbon atoms, allyl alcohol, propargyl alcohol, a $C_3$–$C_7$ cycloalkyl alcohol, a ($C_3$–$C_7$ cycloalkyl) methanol, a 1-($C_3$–$C_7$ cycloalkyl) ethanol, benzyl alcohol, α-methylbenzyl alcohol or phenol, in benzene with an acid scavenger such as pyridine to provide the corresponding ester. The appropriate 3,4-dinitrobenzoic acid ester is then hydrogenated at 60 psi in the presence of a catalyst such as Raney nickel or palladium-on-carbon to provide the corresponding o-phenylenediamine ester. Cyclization of an o-phenylenediamine ester thus obtained yields the 2-aminobenzimidazole esters (II). The cyclization is carried out in the presence of cyanogen bromide as described by Buttle, et. al., Bio Chem, J., 32, 1101 (1938) and British Patent 551,524. The preparation of a variety of benzimidazoles is also well documented in Weissberger's *The Chemistry of Heterocyclic Compounds, Imidazole and Its Derivatives* (Interscience Publisher Co., New York, 1953). Ethyl 2-amino-5(6)-benzimidazole carboxylate is described by Paget, et al., J. Med. Chem. 12, 1010 (1969).

An alternative method for the preparation of 0-phenylenediamine esters begins with 3-nitro-4-chlorobenzoic acid instead of 3,4-dinitrobenzoic acid. Reaction of 3-nitro-4-chlorobenzoic acid as above with oxalyl chloride and pyridine yields 3-Nitro-4-chlorobenzoyl chloride. The appropriate 3-nitro-4chlorobenzoic acid ester is then prepared from the acid chloride as previously described. The 3-nitro-4-chlorobenzoic acid ester is next reacted with dibenzylamine in dimethylformamide at elevated temperatures to give the corresponding 3-nitro-4-dibenzylaminobenzoic acid ester. At this point the nitro dibenzyl ester is hydrogenated catalytically with Raney nickel for example, with concomitant debenzylation and reduction of the nitro group tp provide the corresponding o-phenylenediamine ester. As before, the o-phenylenediamine ester is cyclized by methods know to the benzimidazole art to provide the required benzimidazole reactants (II).

The required haloalkylisothiocyanate reactants optionally substituted with $C_1$–$C_3$ alkyl, benzyl or phenyl groups useful in synthesizing the compounds of this invention are readily prepared from the corresponding haloalkyl amines (V) and thiophosgene:

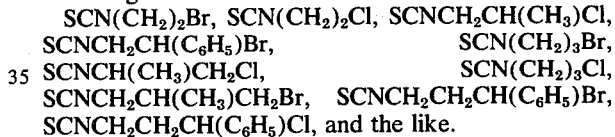

$$X-(CH_2)_n-NH_2 \quad (V) \xrightarrow[\text{base}]{CSCl_2} X-(CH_2)_nNCS \quad (IV)$$

Additional routes for the preparation of haloalkylisothiocyanates (IV) are described in Houben-Weyl's *Methoden Der Organischen Chemie*, Vol. 9 (G. Thieme Verlay Stuttgart, 1955. Examples of haloalkylisothiocyanates which can be employed herein include the following:

$SCN(CH_2)_2Br$, $SCN(CH_2)_2Cl$, $SCNCH_2CH(CH_3)Cl$, $SCNCH_2CH(C_6H_5)Br$, $SCN(CH_2)_3Br$, $SCNCH(CH_3)CH_2Cl$, $SCN(CH_2)_3Cl$, $SCNCH_2CH(CH_3)CH_2Br$, $SCNCH_2CH_2CH(C_6H_5)Br$, $SCNCH_2CH_2CH(C_6H_5)Cl$, and the like.

It will be appreciated by those skilled in the art that advantageous chemical operations can be performed at optional stages of product synthesis. For example a 1-thiazolinyl- or 1-thiazinylbenzimidazole compound can be prepared initially and then be modified chemically to provide the final desired product. In those compounds represented by Formula I wherein $R_2$ is formyl, acetyl or propionyl it is preferred that the acyl function be introduced after the thiazoline or thiazine moiety has been formed.

The compounds of the invention exhibit a broad spectrum of antiviral activity. Not only are they especially effective in inhibiting the growth of echo virus, Mengo, Coxsackie, (A9,21,B5), polio (types I, II, III) or rhinovirus (25 strains) but they also inhibit various types of influenza viruses including influenza strains such as Ann Arbor, Maryland B, Massachusetts B, Hong Kong A, Pr-8a and Taylor C (types A,B). The ability of compounds coming within the scope of Formula I above to suppress the growth of different viruses in vitro is readily demonstrated by using a plaque suppression test similar to that described by Siminoff, *Applied Microbiology*, 9(1), 66–72 (1961). The specific tests are described in detail hereinbelow. The compounds of the invention were tested by the following methods.

TEST METHODS

African green monkey kidney cells (BSC-1) or Hela cells (5-3) were grown in 25 cc. Falcon flasks at 37 C. in medium 199 with 5 percent inactivated fetal bovine serum (FBS), penicillin (150 units 1 ml.) and streptomycin (150 mcg./ml.). When confluent monolayers were formed, the supernatant growth medium was removed and 0.3 ml. of an appropriate dilution of 2-amino-5(6)-alkoxycarbonylbenzimidazole. Columns 3–10 indicate the percentage virus plaque reduction at drug dilutions from 0.75–100 micrograms per milliliter (mcg./ml.).

Table I

Polio I Plaque Reduction of 1-Thiazolinyl(Thiazinyl)-2-Amino-5(6)-alkoxycarbonylbenzimidazoles

| 1-Substituent | 5(6)-Substituent* | \multicolumn{8}{c}{Drug Concentration (mcg/ml)} |
|---|---|---|---|---|---|---|---|---|---|
| | | 100 | 50 | 25 | 12 | 6 | 3 | 1.5 | 0.75 |
| | | \multicolumn{8}{c}{Percent Plaque Reduction} |
| Thiazolin-2-yl | 6-methoxycarbonyl | 100 | 100 | 100 | 100 | 100 | 83 | 45 | 18 |
| Thiazolin-2-yl | 5-ethoxycarbonyl | 100 | 97 | 74 | 44 | 0 | 0 | 0 | 0 |
| Thiazolin-2-yl | 6-ethoxycarbonyl | 100 | 100 | 100 | 100 | 99 | 55 | 16 | 0 |
| Thiazin-2-yl | 5-ethoxycarbonyl | 100 | 99 | 81 | 49 | 18 | 0 | 0 | 0 |
| Thiazin-2-yl | 6-ethoxycarbonyl | 100 | 100 | 100 | 100 | 98 | 66 | 31 | 0 |
| (5-methylthiazolin-2-yl) | 5(6)-ethoxycarbonyl | tox | tox | 100 | 100 | 100 | 100 | 87 | 34 |
| (4-methylthiazolin-2-yl) | 5(6)-ethoxycarbonyl | 100 | 100 | 100 | 100 | 100 | 100 | 70 | 51 |
| (4,5-dimethylthiazolin-2-yl) | 5(6)-ethoxycarbonyl | tox | tox | tox | 100 | 100 | 100 | 100 | 76 |

*Number 5 or 6 indicates respective isomer; 5(6) indicates isomer mixture.

virus (echo, Mengo, Coxsackie, polio or rhinovirus) was added to each flask. After absorption for one hour at room temperature, the virus infected cell sheet was overlaid with a medium comprising one part of 1 percent Ionager No. 2 and one part double strength medium 199 with FBS, penicillin, and streptomycin which contains drug at concentrations of 100, 50, 25, 12, 6, 3, 1.5, and 0.75 micrograms per milliliter (mcg./ml.). The flask containing no drug served as the control for the test. The stock solutions of thiazolinyl or thiazinyl benzimidazole ester compounds were made up in dimethylsulfoxide at a concentration of $10^4$ mcg./mg. The flasks were incubated for 72 hours at 37° C. for polio, Coxsackie, echo, and Mengo virus and 120 at 32° C. for rhinovirus. The influenza virus strains such as, Ann Arbor, Maryland B, Massachusetts B, Hong Kong A, Pr-8a or Taylor C (types A,B), were incubated for 72 hours at 37° C. using MDCK cells (Madin-Darby canine kidney cells). Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration indicated by the symbol $I_{50}$ which inhibits plaque formation by 50 percent can be used as a measure of activity.

Test results are expressed in terms of Polio virus type I inhibition because the virus is easy to grow and consistent test results are obtained. However, the activity of the preferred compounds was confirmed against other virus cultures such as Coxsackie (A9, A21, B5), echovirus (strains 1–4), Mengo, rhinovirus (25 strains Polio (type I, II, III), and influenza virus strains such as Ann Arbor, Maryland B, Massachusetts B, Hong Kong A, Pr-8A and Taylor C (types A, B). Test results for various thiazolinyl or thiazinyl benzimidazole compounds are summarized in Table I below. In the table, column 1 gives the name of substituent in the 1-position and column 2 gives the name of substituent in the 5(6)-position of the corresponding 1-thiazolinyl (thiazinyl)-

The 1-thiazolinyl- or 1-thiazinylbenzimidazole ester compounds were tested both as pure compounds and as isomer mixtures. As can be seen from Table I, both isomers inhibit virus growth, the 6-isomer generally being more active than the 5-isomer.

Compounds coming within the scope of the above formula are able to suppress the growth of several viruses when added to a medium in which the virus is growing. The compounds of the invention can therefore be used in aqueous solution, preferably with a surfactant, to decontaminate surfaces on which polio, Coxsackie, rhinovirus and influenza viruses are present, such surfaces including hospital glassware, hospital working surfaces, and similar areas in the preparation of food.

Furthermore, the compounds can be orally administered to warm-blooded animals and humans in a dose of 1 to 300 mg./kg. of animal body weight. The administration can be repeated periodically as needed. In accordance with general practice, the antiviral compound can be administered every four to six hours.

Preferably, the compounds to be employed in accordance with the present invention are employed in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alignate, sodium benzoate and stearic acid. Such compositions can be formulated as tablets or enclosed in capsules for convenient administration. In addition, the compounds can be administereed parenterally.

The compounds can also be mixed with a liquid and administered as nose drops or intranasal spray.

Among the preferred compounds of the invention are those wherein $R_2$ is hydrogen and $R_3$ is $C_1$–$C_3$ alkyl.

Illustrative of the thiazolinyl or thiazinyl benzimidazole ester compounds included in the scope of this invention are the following:

1-(thiazolin-2-yl)-2-propionamido-5(6)-methoxycarbonylbenzimidazole, 1-(thiazin-2-yl)-2-acetamido-5(6)-ethoxycarbonylbenzimidazole, 1-(thiazolin-2-yl)-2-formamido-5(6)-propoxycarbonylbenzimidazole,
1-(thiazin-2-yl)-2-amino-5(6)-butoxycarbonylbenzimidazole,
1-(thiazolin-2-yl)-2-propionamido-5(6)-pentyloxycarbonylbenzimidazole,
1-(4-propylthiazolin-2-yl)-2-acetamido-5(6)-hexyloxycarbonylbenzimidazole,
1-(5-benzylthiazin-2-yl)-2-formamido-5(6)-octyloxycarbonylbenzimidazole,
1-(6-methylthiazin-2-yl)-2-propionamido-5(6)-pentyloxycarbonylbenzimidazole,
1-(4-phenylthiazolin-2-yl)-2-acetamido-5(6)-butoxycarbonylbenzimidazole,
1-(thiazin-2-yl)-2-formamido-5(6)-propoxycarbonylbenzimidazole,
1-(4-ethylthiazolin-2-yl)-2-amino-5(6)-ethoxycarbonylbenzimidazole,
1-(4-ethylthiazin-2-propionamido-5(6)-methoxycarbonylbenzimidazole,
1-(thiazolin-2-yl)-2-acetamido-5(6)-ethoxycarbonylbenzimidazole,
1-(thiazin-2-yl)-2-formamido-5(6)-propoxycarbonylbenzimidazole,
1-(5-methylthiazolin-2-yl)-2-amino-5(6)-butoxycarbonylbenzimidazole,
1-(6-benzylthiazin-2-yl)-2-propionamido-5(6)-octyloxycarbonylbenzimidazole,
1-(thiazolin-2-yl)-2-acetamido-5(6)-pentyloxycarbonylbenzimidazole,
1-(5-methylthiazin-2-yl)-2-formamido-5(6)-propoxycarbonylbenzimidazole,
1-(4-benzylthiazolin-2-yl)-2-amino-5(6)-methoxycarbonylbenzimidazole,
1-(thiazin-2-yl)-2-propionamido-5(6)-ethoxycarbonylbenzimidazole,
1-(5-propythiazolin-2-yl)-2-acetamido-5(6)-pentyloxycarbonylbenzimidazole,
1-(thiazin-2-yl)-2-formamido-5(6)-hexyloxycarbonylbenzimidazole,
1-(thiazolin-2-yl)-2-amino-5(6)-methoxycarbonylbenzimidazole,
1-(5-phenylthiazin-2-yl)-2-propionamido-5(6)-propoxycarbonylbenzimidazole,
1-(4-phenylthiazolin-2-yl) -acetamido-5(6-octyloxycarbonylbenzimidazole,
1-(thiazin-2-yl)-2-formamido-5(6)-ethoxycarbonylbenzimidazole
1-(5-benzylthiazolin-2-yl)-2-amino-5(6)-propoxycarbonylbenzimidazole,
1-(4-propylthiazin-2-yl)-2-propionamido-5(6)-hexyloxycarbonylbenzimidazole,
1-(thiazolin-2-yl)-2-acetamido-5(6)-propoxycarbonylbenzimidazole,
1-(thiazin-2-yl)-2-formamido-5(6)-methoxycarbonylbenzimidazole,
1-(4-methylthiazolin-2-yl)-2-amino-5(6)-octyloxycarbonylbenzimidazole,
1-(thiazin-2-yl)-2-propionamido-5(6)-ethoxycarbonylbenzimidazole,
1-(thiazin-2-yl)-2-acetamido-5(6)-butoxycarbonylbenzimidazole,
1-(4-propylthiazin-2-yl)-2-formamido-5(6)-octyloxycarbonylbenzimidazole,
1-(5-benzylthiazolin-2-yl)-2-amino-5(6)-heptyloxycarbonylbenzimidazole,
1-(thiazin-2-yl)-2-propionamido-5(6)-methoxycarbonylbenzimidazole,
1-(thiazolin-2-acetamido-5(6)-propoxycarbonylbenzimidazole,
1-(5-propylthiazin-2-formamido-5(6)-ethoxycarbonylbenzimidazole,
1-(4-phenylthiazin-2-yl)-2-amino-5(6)-heptyloxycarbonylbenzimidazole,
1-(thiazin-2-yl)-2-propionamido-5(6)-butoxycarbonylbenzimidazole,
1-(thiazolin-2-yl)-2-acetamido-5(6)-ethoxycarbonylbenzimidazole,
1-(6-propylthiazin-2-yl)-2-formamido-5(6)-propoxycarbonylbenzimidazole,
1-(5-benzylthiazolin-2-yl)-2-amino-5(6)-hexyloxycarbonylbenzimidazole,
1-(thiazin-2-yl)-2-propionamido-5(6)-pentyloxycarbonylbenzimidazole,
1-(thiazolin-2-yl)-2-acetamido-5(6)-heptyloxycarbonylbenzimidazole,
1-(6-methylthiazin-2-yl)-2-formamido-5(6)-methoxycarbonylbenzimidazole,
1-(5-methylthizaolin-2-amino-5(6)-heptyloxycarbonylbenzimidazole,
1-(thiazin-2-yl)-2-propionamido-5(6)-octyloxycarbonylbenzimidazole,
1-(5-phenylthiazolin-2-yl)-2-amino-5(6)-methoxycarbonylbenzimidazole,
1-(4-benzylthiazolin-2-yl)-2-formamido-5(6)-butoxycarbonylbenzimidazole,
1-(5-propylthiazolin-2-yl)-2-acetamido-5(6)-methoxycarbonylbenzimidazole,
1-(4-methylthiazolin-2-yl)-2-propionamido-5(6)-pentyloxycarbonylbenzimidazole,
1-(5-ethylthiazolin-2-yl)-2-amino-5(6)-heptyloxycarbonylbenzimidazole,
1-(4-phenylthiazole-2-yl)-2-propionamido-5(6)-ethoxycarbonylbenzimidazole,
1-(5-methylthiazol-2-yl)-2-acetamido-5(6)-butoxycarbonylbenzimidazole, 1-(thiazolin-2-yl)-2-formamido-5(6)-propoxycarbonylbenzimidazole,
1-(4-methylthiazolin-2-yl)-2-amino-5(6)-pentyloxycarbonylbenzimidazole,
1-(5-phenylthiazolin-2-yl)-2-propionamido-5(6)-octyloxycarbonylbenzimidazole,
1-(4-ethylthiazolin)-2-acetamido-5(6)-ethoxycarbonylbenzimidazole,
1-(5-propylthiazolin-2-yl)- 2-amino-5(6)-methoxycarbonylbenzimidazole,
1-(thiazolin-2-yl)-2-propionamido-5(6)-hexyloxycarbonylbenzimidazole,
1(4-propylthiazolin-2-yl)-2-amino-5(6)-octyloxycarbonylbenzimidazole,
1-(thiazolin-2-yl)-2-propionamido-5(6)-heptyloxycarbonylbenzimidazole, 1-(5-benzylthiazolin-2-yl)-2-acetamido-5(6)-octyloxycarbonylbenzimidazole,
1-(thiazolin-2-yl)-2-formamido-5(6)-hexyloxycarbonylbenzimidazole, 1-(5-propylthiazolin-2-yl)-2-amino-5(6)-butoxycarbonylbenzimidazole,
1-(thiazolin-2-yl)-2-propionamido-5(6)-ethoxycarbonylbenzimidazole,
1-(5-methylthiazolin-2-yl)-2-acetamido-5(6)-methoxycarbonylbenzimidazole,
1-(thiazolin-2-formamido-5(6)-propoxycarbonylbenzimidazole,
1-(4-ethylthiazolin-2-yl)-2-amino-5(6)-pentyloxycarbonylbenzimidazole,
1-(thiazolin-2-yl)-2-propionamido-5(6)-heptyloxycarbonylbenzimidazole, 1-(thiazin-2-yl)-2-acetamido-5(6)-ethoxycarbonylbenzimidazole,
1-(6-phenylthiazin-2-yl)-2-formamido-5(6)-butoxycarbonylbenzimidazole,
1-(4-methylthiazin-2-yl)-2-amino-5(6)-propoxycarbonylbenzimidazole,
1-(5-propylthiazin-2-yl)-2-propionamido-5(6)-pentyloxycarbonylbenzimidazole,
1-(4-benzylthiazin-2-acetamido-5(6)-hexyloxycarbonylbenzimidazole,
1-(thiazolin-2-yl)-2-formamido-5(6)-heptyloxycarbonylbenzimidazole,
1-(5-propylthiazin-2-yl)-2-amino-5(6)-octyloxycarbonylbenzimidazole,
1-(4-ethylthiazin-2-yl)-2-propionamido-5(6)-methoxycarbonylbenzimidazole,
1-(thiazin-2-yl)-2-acetamido-5(6)-methoxycarbonylbenzimidazole,
1-(6-methylthiazin-2-yl)-2-formamido-5(6)-propoxycarbonylbenzimidazole,
1-(4-ethylthiazin-2-yl-2-amino-5(6)-pentyloxycarbonylbenzimidazole,
1-(thiazolin-2-yl)-2-propionamido-5(6)-heptyloxycarbonylbenzimidazole,
1-(5-propylthiazin-2-yl)-2-acetamido-5(6)-octyloxycarbonylbenzimidazole,
1-(4-propylthiazolin-2-yl)-2-formamido-5(6)-hexyloxycarbonylbenzimidazole, 1-(thiazolin-2-yl)-2-amino-5(6)-butoxycarbonylbenzimidazole,
1-(thiazin-2-yl)-2-propionamido-5(6)-ethoxycarbonylbenzimidazole,
1-(5-ethylthiazolin-2-yl)-2-acetamido-5(6)-heptyloxycarbonylbenzimidazole,
1-(5-benzylthiazin-2-yl)-2-formamido-5(6)-pentyloxycarbonylbenzimidazole,
1-(thiazolin-2-yl)-2-amino-5(6)-propoxycarbonylbenzimidazole,
1-(4-phenylthiazin-2-yl)-2-propionamido-5(6)-methoxycarbonylbenzimidazole,
1-(5-methylthiazolin-2-yl)-2-acetamido-5(6)-octyloxycarbonylbenzimidazole,
1-(4-propylthiazin-2-yl)-2-formamido-5(6)-hexyloxycarbonylbenzimidazole,
1-(5-ethylthiazolin-2-yl)-2-propionamido-5(6)-butoxycarbonylbenzimidazole,
1-(thiazin-2-yl)-2-acetamido-5(6)-ethoxycarbonylbenzimidazole,
1-(4-benzylthiazolin-2-yl)-2-formamido-5(6)-heptyloxycarbonylbenzimidazole,
1-(4-methylthiazin-2-yl)-2-amino-5(6)-propoxycarbonylbenzimidazole,
1-(thiazolin-2-yl)-2-propionamido-5(6)-pentyloxycarbonylbenzimidazole,
1-(5-phenylthiazin-2-yl)-2-acetamido-5(6)-heptyloxycarbonylbenzimidazole,
1-(4-propylthiazolin-2-yl)-2-formamido-5(6)-hexyloxycarbonylbenzimidazole,
1-(thiazolin-2-yl)-2-formamido-5(6)-(1-cyclopropylethoxy)carbonylbenzimidazole,
1-(4-methylthiazolin-2-yl)-2-amino-5(6)-cyclobutyloxycarbonylbenzimidazole,
1-(5-phenylthiazolin-2-yl)-2-propionamido-5(6)-cyclobutylmethoxycarbonylbenzimidazole,
1-(4-ethylthiazolin-2-yl)-2-acetamido-5(6)-(1-cyclobutylethoxy)carbonylbenzimidazole,
1-(5-propylthiazolin-2-yl)-2-amino-5(6)-cyclopentyloxycarbonylbenzimidazole,
1-(thiazolin-2-yl)-2-propionamido-5(6)-cyclopentylmethoxycarbonylbenzimidazole,
1-(4-propylthiazolin-2-yl)-2-amino-5(6)-(1-cyclopentylethoxy)carbonylbenzimidazole,
1-(thiazolin-2-yl)-2-propionamido-5(6)-cyclohexyloxycarbonylbenzimidazole,
1-(5-benzylthiazolin-2-yl)-2-acetamido-5(6)-cyclohexylmethoxycarbonylbenzimidazole,
1-(thiozolin-2-yl)-2-formamido-2-formamido-5(6)-(1-cyclohexylethoxy)carbonylbenzimidazole,
1-(5-propylthiazolin-2-yl)-2-amino-5(6)-cycloheptyloxycarbonylbenzimidazole,
1-(thiazolin-2-yl)-2-propionamido-5(6)-cycloheptylmethoxycarbonylbenzimidazole,
1-(5-methylthiazolin-2-yl)-2-acetamido-5(6)-(1-cycloheptylexthoxy)carbonylbenzimidazole,
1-(thiazolin-2-yl)-2-formamido-5(6)-cycloheptyloxycarbonylbenzimidazole,
1-(4-ethylthiazolin-2-yl)-2-amino-5(6)-cycloheptylmethoxycarbonylbenzimidazole, 1-(thiazolin-2-yl)-2-propionamido-5(6)-(1-cycloheptylethoxy)carbonylbenzimidazole,
1-(thiazin-2-yl)-2-acetamido-5(6)-cyclopropyloxycarbonylbenzimidazole,
1-(6-phenylthiazin-2-yl)-2-formamido-5(6)-cyclopropylmethoxycarbonylbenzimidazole,
1-(4-methylthiazin-2-yl)-2-amino-5(6)-(1-cyclopropylethoxy)carbonylbenzimidazole,
1-(5-propylthiazin-2-yl)-2-propionamido-5(6)-cyclobutyloxycarbonylbenzimidazole,
1-(4-benzylthiazin-2-yl)-2-acetamido-5(6)-cyclobutylmethoxycarbonylbenzimidazole,
1-(thiazolin-2-yl)-2-formamido-5(6)-(1-cyclobutylethoxy)carbonylbenzimidazole,
1-(5-propylthiazin-2-yl)-2-amino-5(6)-cyclopentyloxycarbonylbenzimidazole,
1-(4-ethylthiazin-2-yl)-2-propionamido-5(6)-cyclopentylmethoxycarbonylbenzimidazole,
1-(thiazin-2-yl)-2-acetamido-5(6)-(1-cyclopentylethoxy)carbonylbenzimidazole,
1-(6-methylthiazin-2-yl)-2-formamido-5(6)-cyclohexyloxycarbonylbenzimidazole,
1-(4-ethylthiazin-2-yl)-2-amino-5(6)-cyclohexylmethoxycarbonylbenzimidazole,
1-(thiazolin-2-yl)-2-propionamido-5(6)-(1-cyclohexylethoxy)carbonylbenzimidazole,
1-(5-propylthiazin-2-yl)-2-acetamido-5(6)-cyclopropyloxycarbonylbenzimidazole,
1-(4-propylthiazolin-2-yl)-2-formamido-5(6)-cyclopropylmethoxycarbonylbenzimidazole,
1-(thiazolin-2-yl)-2-amino-5(6)-cyclopropyloxycarbonylbenzimidazole,
1-(thiazin-2-yl)-2-propionamido-5(6)-cyclopropylmethoxycarbonylbenzimidazole,
1-(5-ethylthiazolin-2-yl)-2-acetamido-5(6)-(1-cyclopropylethoxy)carbonylbenzimidazole,
1(5-benzylthiazin-2-yl)-2-formamido-5(6)-cyclobutyloxycarbonylbenzimidazole,
1-(thiazolin-2-yl)-2-amino-5(6)-cyclobutylmethoxycarbonylbenzimidazole,
1-(4-phenylthiazin-2-yl)-2-propionamido-5(6)-cyclopentylmethoxycarbonylbenzimidazole,
5-methylthiazolin-2-yl)-2-acetamido-5(6)-(1-)cyclobutylethoxy)carbonylbenzimidazole,
1-(4-propylthiazin-2-yl)-2-formamido-5(6)-cyclopentyloxycarbonylbenzimidazole,
1-(5-ethylthizaolin-2-yl)-2-propionamido-5(6)-cyclopentylmethoxycarbonylbenzimidazole, 1-

(thiazin-2-yl)-2-acetamido-5(6)-1-cyclopentylethoxy)carbonylbenzimidazole,
1-(4-benzylthiazolin-2-yl)-2-formamido-5-(6)-cyclohexyloxycarbonylbenzimidazole,
1-(4-methylthiazin-2-amino-5(6)-cyclohexylmethoxycarbonylbenzimidazole,
1-(thiazolin-2-yl)-2-propionamido-5(6)-1-cyclohexylethoxy)carbonylbenzimidazole,
1-(5-phenylthiazin-2-yl)-2-acetamido-5(6)-cycloheptoxycarbonylbenzimidazole,
1-(4-propylthiazolin-2-yl)-2-formamido-5(6)-cycloheptylmethoxycarbonylbenzimidazole, 1-(thiazolin-2-yl)-2-acetamido-5(6-(1-cycloheptylethoxy)carbonylbenzimidazole,
1-(6-propylthiazin-2-yl)-2-formamido-5(6)-cyclobutyloxycarbonylbenzimidazole,
1-(5-benzylthiazolin-2-yl)-2-amino-5(6)-cyclopentylmethoxycarbonylbenzimidazole,
1-(thiazin-2-yl)-2-propionamido-5(6)-(1-cyclohexylethoxy)-carbonylbenzimidazole,
1-(thiazolin-2-yl)-2-acetamido-5(6)-cycloheptyloxycarbonylbenimidazole,
1-(6-methylthiazin-2-yl)-2-formamido-5(6)-(1-cyclohepylethoxy)carbonylbenzimidazole,
1-(5-methylthiazolin-2-yl)-2-amino-5(6)-cyclobutyloxycarbonylbenzimidazole,
1-(thiazin-2-yl)-2-propionamido-5(6)-t-butyloxycarbonylbenzimidazole,
1-(5-phenylthiazolin-2-yl)-2-amino-5(6)-t-butyloxycarbonylbenzimidazole,
1-(4-benzylthiazolin-2-yl)-2-formamido-5(6)-t-butyloxycarbonylbenzimidazole,
1-(5-propylthiazolin-2-yl)-2-acetamido-5(6)-t-butyloxycarbonylbenzimidazole,
1-(4-methylthiazolin-2-yl)-2-propionamido-5(6)-isobutyloxycarbonylbenzimidazole,
1-(5-ethylthiazolin-2-yl)-2-amino-5-(6)-s-butyloxycarbonylbenzimidazole,
1-(4-phenylthiazole-2-yl)-2-propionamido-5(6)-t-butyloxycarbonylbenzimidazole,
1-(5-methylthiazol-2-yl)-2-acetamido-5(6)-t-butyloxycarbonylbenzimidazole,
1-(thiazin-2-yl)-2-amino-5(6)-propoxycarbonylbenzimidazole,
1-(thiazolin-2-yl)-2-propionamido-5-(6)-methoxycarbonylbenzimidazole,
1-(6-methylthiazin-2-yl)-2-acetamido-5(6)-ethoxycarbonylbenzimidazole,
1-(5-benzylthiazolin-2-formamido-5(6)-butoxycarbonylbenzimidazole,
1-(5-methylthiazin-2-yl)-2-amino-5(6)-hexyloxycarbonylbenzimidazole,
1-(4-ethylthiazolin-2-yl)-2-propionamido-5(6)-heptyloxycarbonylbenzimidazole,
1-(thiazin-2-yl)-2-acetamido-5(6)-octyloxycarbonylbenzimidazole,
1-5-propylthiazolin-2-yl)-2-formamido-5(6butoxylcarbonyl, and
1-(4-phenylthiazin-2-yl)-2-amino-5(6)-methoxycarbonylbenzimidazole.

The following examples illustrate further the preparation of starting materials, intermediates, and compounds of the invention.

EXAMPLES 1-4

1-Thiazolinyl(thiazinyl)-2-amino-5(6)-ethoxycarbonylbenzimidazoles (General Procedure).

Fifty-four grams (0.265 mole) of 2-amino-5(6)-ethoxycarbonylbenzimidazole were suspended in 500 ml. of ethylene glycol dimethyl ether (dimethoxyethane, DME). Thirteen grams (0.27 mole) of sodium hydride as a 50 percent mineral oil suspension was added to the stirred reaction mixture in portions to generate the benzimidazole anion. A solution of 33 g. (0.27 mole) of β-chloroethylisothiocyanate in 50 ml. of dimethoxyethane was added dropwise to the reaction mixture with ice bath cooling to moderate the exothermic reaction. The reaction mixture was stirred overnight at room temperature. The precipitated product was filtered and washed successively with DME, water and ether. After dying the crude yield of product as an isomeric mixture was 52 g (67.5 percent yield). The product was dissolved in 2 liters of 2B ethanol and filtered. The filtrate was concentrated by boiling and the product isomers were isolated by fractional crystallization. The yield of 1-(thiazolin-2-yl)-2-amino-5-ethoxycarbonylbenzimidazole was 12 g. The yield of 1--(thiazolin-2-yl)-2-amino-6-ethoxycarbonylbenzimidazole was 22.4 g.

Analysis $C_{13}H_{14}N_4O_2S$ MW 290. Calcd: C, 53.78; H, 4.86; N, 19.30; Found: 5-isomer: C, 53.85; H, 5.02; N, 19.07. 6-isomer: C, 53.62; H, 4.64; N, 19.07.

The following compounds were prepared by the method described above using 2-amino-5(6)-ethoxycarbonylbenzimidazole and 2-chloro-1-methylethylisothicyanate (Ex. 2), 2-chloropropylisothiocyante (Ex 3), and 3-chloropropylisothiocyanate (Ex. 4).

1-(4-methylthiazolin-2-yl)-2-amino-5(6)-ethoxycarbonylbenzimidazole as an isomeric mixture, yield 5.5 g (52 percent) from 7.2 g. (0.035 mole) of benzimidazole ester.

Analysis $C_{14}H_{15}N_4O_2S$ MW 303; Calcd: C, 55.43; H, 4.98; N, 18.47. Found: C, 55.47; H. 5.14; N, 18.81.

1-(5-methylthiazolin-2-yl)-2-amino-5(6)-ethoxycarbonylbenzimidazole as an isomeric mixture, yeild 4.5 g (42 percent) from 7.2 g (0.035 mole) of benzimidazole ester.

Analysis $C_{14}H_{15}N_2S$ MW 303; Calcd: C, 55.43; H, 4.98; H, 18.47. Found: C, 55.06; H, 5.22; N, 18.16.

1-(thiazin-2-yl)-2-amino-5(6)-ethoxycarbonylbenzimidazole from 7.2 g (0.035 mole) of benzimidazole ester. The isomers were fractionally crystallized from ethyl acetate.

Analysis $C_{14}H_{16}N_4O_2S$ MW 304; Calcd: C, 55.25; H, 5.30; N, 18.41. Found: 5-isomer: C, 55.40; H, 5.16; N, 18.19. 6-isomer: C, 55.02; H, 5.23; N, 18.13.

The yield of 5-isomer, mp 157°–160° C, was 0.9 g. The yield of 6-isomer, mp 163°–166° C, was 2.3 g.

EXAMPLE 5

1-(Thiazolin-2-yl)-2-amino-6-methoxycarbonylbenzimidazole 1-(thiazolin-2-yl)-2-amino-6-(1-imidazolylcarbonyl)benzimidazole was prepared from 1-(thiazolin-2-yl)-2-amino-6-benzimidazole carboxylic acid and 1, 1'-carbonylbisimidazole. One and three-tenths grams (4.2 mmole) of 1-(thiazolin-2-yl)-2-amino-6-(1-imidazolylcarbonyl)benzimidazole were heated on the steam bath with 25 ml of methanol and 15 ml of dimethylformamide until the solution became homogenous. The reaction mixture was evaporated in vacuo to leave a residue. Water was added to the residue and the insoluble product was filtered to yield 700 mg. of 1-(thiazolin-2-yl)-2-amino-6-methoxycarbonylbenzimidazole, mp 209°–211° C.

Analysis $C_{12}H_{12}N_4O_2S$ MW 276; Calcd: C, 52.16; H, 4.38; N, 20.28. Found: C, 51.99; H, 4.16; N, 20.08.

EXAMPLE 6

1-(Thiazolin-2-yl)-2-Amino-6-Cyclohexyloxycarbonyl-benzimidazole (A)Cyclohexyl 3-nitro-4-chlorobenzoate Ten grams (0.05 mole) of 3-nitro-4-chlorobenzoic acid, 50 ml. of benzene, 13 g (0.1 mole) of oxalyl chloride and 3 drops of pyridine were stirred at room temperature for about 1 hour. The mixture was warmed to 55° C to obtain a homogeneous solution. The reaction mixture was evaporated in vacuo to yield an oil. Under vacuum the oil crystallized to yield 12 g. of 3-nitro-4-chlorobenzoyl chloride.

Twelve grams (0.055 mole) of crude-3-nitro-4-chlorobenzoyl chloride were dissoved in 200 ml. of benzene. Eight milliliters of pyridine were added to the reaction mixture. Six milliliters of cyclohexanol were dissolved in 50 ml. of benzene and the solution was added dropwise to the acid chloride-pyridine mixture. The reaction mixture was refluxed for 4 hours and filtered. The benzene filtrate was washed successively with dilute acid, dilute base and water. The benzene solution was dried and evaporated in vacuo to yield 12.5 g. (88 percent) of cyclohexyl 3-nitro-4-chlorobenzoate, mp 57°–58° C.

Analysis $C_{13}H_{24}ClNO_4$ MW 283.5; Calcd: C, 55.04; H, 4.97; n, 4.94. Found: C, 54.90; H, 5.15; N, 5.14.

(B)Cyclohexyl 3-nitro-4-dibenzylaminobenzoate

Two and eight-tenths grams (0.01 mole) of cyclohexyl 3-nitro-4-chlorobenzoate, 4.4 ml. (0.022 mole) of dibenzylamine and 20 ml. of dimethylformamide (DMF) were refluxed for 6 hours. The reaction mixture was evaporated in vacuo and the residue was diluted with 500 ml. of water. The aqueous mixture was extracted with ethyl acetate. The ethyl acetate solution was dried and evaporated in vacuo to give an oil. The oil was taken up in ether and filtered. The solution was evaporated in vacuo to yield 4.2 g. (95 percent) of cyclohexyl 3-nitro-4-dibenzylaminobenzoate as an oil.

(C) 2-Amino-5(6)-cyclohexyloxycarbonylbenzimidazole

One hundred grams (0.386 mole) of cyclohexyl 3-nitro-4-dibenzylaminobenzoate were hydrogenated at 60° C for 22 hours with 25 g. of palladium-on-carbon in 875 ml. of 2B ethanol. The catalyst was filtered and the filtrate was evaporated in vacuo to leave an oil. The oil was taken up in ethyl acetate and filtered. Anhydrous HCl gas was passed over the surface of the ethyl acetate solution with stirring. The precipitated o-phenylenediamine hydrochloride salt was collected and washed with anhydrous ether to yield 24.3 g. of product. The salt was dissolved in water and the pH of the aqueous solution was adjusted to 7.00 with 1N sodium hydroxide (130 ml.). Forty milliliters of methanol and 9 g. (0.0845 mole) of cyanogen bromide were added to the aqueous solution. The reaction mixture was stirred overnight. The aqueous mixture was basified in 1N sodium hydroxide and extracted with ethyl acetate. The ethyl acetate extract was decolorized with carbon and filtered. The ethyl acetate solution was evaporated in vacuo to yield 16 b. (73 percent yield based on cyanogen bromide) of 2-amino-5(6)-cyclohexyloxycarbonylbenzimidazole as an oil.

(D)1-(Thiazolin-2-yl)-2-amino-6-cyclohexyloxycarbonylbenzimidazole

Seven and eight-tenths grams (0.03 mole) of 2-amino-5(6)-cyclohexyloxycarbonylbenzimidazole, 100 ml. of demethoxyethane (glyme), 1.5 g. of sodium hydride as a 50 percent mineral dispersion, and 3.7 g. (0.03 mole) of β-chloroethylisothiocyanate were reacted by the method of Example 1 to yield 1.2 g. of 1-(thiazolin-2-yl)-2-amino-6-cyclohexyloxycarbonylbenzimidazole, mp 231°–232° C (methanol).

Analysis $C_{17}H_{20}N_4O_2S$ MW 344; Calcd- C, 59.28; H, 5.85; N, 16.27. Found: C, 59.06; H, 5.72; N, 16.47.

Examples 7–9

1-(Thiazolin-2-yl)-2-amino-5(6)-isopropyloxycarbonylbenzimidazole was prepared from 2-amino-5(6)-isopropyloxycarbonylbenzimidazole via isopropy 3-nitro-4-chlorobenzoate by the method of Example 6. Six and six-tenths grams (0.03 mole) of the benzimidazole above, 100 ml. of dimethoxyethane, 1.5 g. of 50 percent sodium hydride and 3.7 g. of β-chloroethylisothiocyanate were reacted to yield 3 g. of 1-(thiazolin-2-yl)-2-amino-5(6)-isopropyloxycarbonylbenzimidazole.

Analysis $C_{14}H_{16}N_4O_2S$ MW 304; Calcd: C, 55.25; H, 5.30; N, 18.41. Found: C, 55.05; H, 5.23; N, 18.37.

1-(Thiazolin-2-yl)-2-amino-6-neopentyloxycarbonylbenzimidazole was prepared by reacting 9.9 g. (40 mmole) of 2-amino-5(6)-neopentyloxycarbonylbenzimidazole (via neopentyl 3-nitro-4-chlorobenzoate), 2.0 g. of 50 percent sodium hydride, 200 ml. of dimethoxyethane and 4.9 g. of β-chloroethylisothiocyanate by the method of Example 6 to yield 1.54 g. of the 6-isomer, mp. 236°–8° C (dec).

Analysis $C_{15}H_{20}N_4O_2S$ MW 332; Calcd: C, 57.83; H, 6.02; N, 16.86. Found: C, 57.75; H. 5.85; N, 16.82.

1-(Thiazolin-2-yl)-2-amino-6-phenoxycarbonylbenzimidazole was prepared by reacting 10.2 g. (90 mmoles) of 2-amino-5(6)-phenoxycarbonylbenzimidazole (via phenyl 3-nitro-4-chlorobenzoate, 170 ml. of dimethoxyethane, 2.0 g. of 50 percent sodium hydride and 4.9 g. of β-chloroethylisothiocyanate by the method of Example 6 to yield 3.2 g. of the 6-isomer, mp 225°–6° C (dec).

Analysis $C_{17}H_{14}N_4O_2S$ MW 338; Calcd: C, 60.34; H, 4.17; N, 16.56. Found: C, 60.13; H, 4.22; N, 16.30.

EXAMPLE 10

1-(Thiazolin-2-yl)-2-Amino-6-t-Butyloxycarbonylbenzimidazole (A)t-Butyl 3,4-Dinitrobenzoate Fifty-three grams (0.25 mole) of 3,4-dinitrobenzoic acid, 500 ml. of benzene, 65 g. (0.51 mole) of oxalyl chloride and 1 ml. of pyridine were reacted according to Example 6 (A), first paragraph, to provide 3,4-dinitrobenzoyl chloride as a crude oil.

The crude 3,4-dinitrobenzoyl chloride, 500 ml. of benzene, 25 ml. of pyridine and 22 g. (0.30 of t-butyl alcohol were reacted as in Example 6 (A), second paragraph, to provide 33 g. (49 percent yield) of t-butyl 3,4-dinitrobenzoate.

Analysis $C_{11}H_{12}N_2O_6$ MW 268; Calcd: C, 49.26; H, 4.51; N, 10.44. Found: C, 48.95; H, 4.30; N, 10.14.

(B)2-Amino-5(6)-t-Butyloxycarbonylbenzimidazole

Four and two-tenths grams (0.02 mole) of t-butyl 3,4-dinitrobenzoate were hydrogenated in 95 ml. of ethanol with 1g. of 5 percent palladium-on-carbon for one hour at room temperature. The exothermic reaction reached a maximum temperature of 45° C with a hydrogen uptake which was 85 percent of theoretical. The catalyst was filtered and the filtrate was evaporated in vacuo to a residual oil. The crude t-butyl 3,4-diaminobenzoate product (0.017 mole) was taken up in a mixture of 20 ml. of methanol and 200 ml. of water. Cyanogen bromide, 1.8 g. (0.017 mole), was reacted with the diamine ester according to the method of Example 6(C) to yield 1.5 g. (38 percent) of 2-amino-5(6)-t-butyloxycarbonylbenzimidazole.

(C) 1-(Thiazolin-2-yl)-2-Amino-6-t-Butyloxycarbonylbenzimidazole

Three grams (13 mmole) of 2-amino-5(6)-t-butyloxycarbonylbenzimidazole, 100 ml. of dimethoxyethane, 0.7 g. of 50 percent sodium hydride, and 1.8 g of β-chlorethylisothiocyanate were reacted by the method of Example 1 to yield 300 mg. of the 6-isomer, 1-(thiazolin-2-yl)-2-amino-6-t-butyloxycarbonylbenzimidazole, mp, 218°–219° C.

Analysis $C_{15}H_{18}N_4O_2S$ MW 318; Calcd: C, 56.58; H. 5.70; N, 17.60. Found: C, 56.80; H, 5.92; N, 17.61.

We claim:

1. A compound of the formula

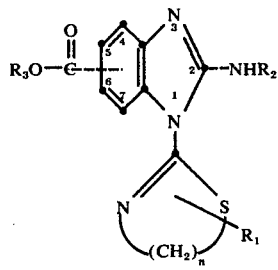

wherein $R_1$ is hydrogen or $C_1$–$C_3$ alkyl;

$R_2$ is hydrogen, formyl, acetyl or propionyl;

$R_3$ is $C_1$–$C_8$ alkyl, $C_3$–$C_7$ cycloalkyl, ($C_3$–$C_7$ cycloalkyl)methyl, 1-($C_3$–$C_7$ cycloalkyl)ethyl, benzyl or α-methylbenzyl;

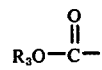

is at the 5 or 6 position; and $n$ is 2 or 3.

2. A compound of claim 1 wherein $R_1$ is hydrogen or methyl, $R_2$ is hydrogen, $R_3$ is $C_1$–$C_8$ alkyl or $C_3$–$C_7$ cycloalkyl, and $n$ is 2.

3. The compound of claim 2 which is 1-(thiazolin-2-yl)-2-amino-5(6)-ethoxycarbonylbenzimidazole.

4. The compound of claim 2 which is 1-(thiazolin-2-yl)-2-amino-5(6)-isopropoxycarbonylbenzimidazole.

5. The compound of claim 2 which is 1-(4-methylthiazolin-2-yl)-2-amino-5(6)-ethoxycarbonylbenzimidazole.

6. The compound of claim 2 which is 1(5-methylthiazolin-2-yl-5(6)-ethoxycarbonylbenzimidazole.

7. The compound of claim 2 which is 1-(thiazolin-2-yl)-2-amino-5(6)-t-butyloxycarbonylbenzimidazole.

8. The compound of claim 2 which is 1-(thiazolin-2-yl)-2-amino-5(6)-neopentyloxycarbonylbenzimidazole.

9. The compound of claim 2 which is 1-(thiazolin-2-yl)-2-amino-5(6)-cyclobutyloxycarbonylbenzimidazole.

10. A compound of claim 2 wherein

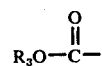

is at the 6 position.

11. The compound of claim 10 which is 1-(thiazolin-2-yl)-2-amino-6-ethoxycarbonylbenzimidazole.

12. The compound of claim 10 which is 1-(thiazolin-2-yl)-2-amino-6-isopropoxycarbonylbenzimidazole.

13. The compound of claim 10 which is 1-(thiazolin-2-yl)-2-amino-6-t-butyloxycarbonylbenzimidazole.

14. The compound of claim 10 which is 1-(thiazolin-2-yl)-2-amino-6-neopentylcarbonylbenzimidazole.

15. The compound of claim 10 which is 1-(thiazolin-2-yl)-2-amino-6-cyclobutyloxycarbonylbenzimidazole.

* * * * *